(12) United States Patent
Lepple-Wienhues

(10) Patent No.: US 7,611,861 B2
(45) Date of Patent: Nov. 3, 2009

(54) METHOD AND APPARATUS FOR PATCH-CLAMP MEASUREMENTS ON CELLS

(75) Inventor: Albrecht Lepple-Wienhues, Tuebingen (DE)

(73) Assignee: Flyion GmbH, Tuebingen (DE)

( * ) Notice: Subject to any disclaimer, the term of this patent is extended or adjusted under 35 U.S.C. 154(b) by 0 days.

(21) Appl. No.: 10/110,751

(22) PCT Filed: Jul. 31, 2001

(86) PCT No.: PCT/EP01/08831

§ 371 (c)(1), (2), (4) Date: Jul. 9, 2002

(87) PCT Pub. No.: WO02/10747

PCT Pub. Date: Feb. 7, 2002

(65) Prior Publication Data

US 2003/0022268 A1    Jan. 30, 2003

(30) Foreign Application Priority Data

Jul. 31, 2000   (EP) .................................. 00116515

(51) Int. Cl.
- C12Q 1/24 (2006.01)
- C12M 1/34 (2006.01)
- G01N 33/48 (2006.01)

(52) U.S. Cl. .................. 435/30; 435/287.1; 435/288.5; 436/63

(58) Field of Classification Search .............. 435/287.1, 435/258.2, 285.3, 288.4, 288.5, 29, 30, 32, 435/33, 173.5, 173.6; 204/403.1–403.03; 205/777.5; 324/450, 692; 436/63

See application file for complete search history.

(56) References Cited

U.S. PATENT DOCUMENTS

| | | |
|---|---|---|
| 3,714,565 A | 1/1973 | Coulter et al. |
| 4,055,799 A | 10/1977 | Coster et al. |
| 4,253,058 A | 2/1981 | Kachel et al. |

(Continued)

FOREIGN PATENT DOCUMENTS

DE    36 26 600    3/1987

(Continued)

OTHER PUBLICATIONS

Hamill et al.'Improved Patch-Clamp Techniques for High-Resolution Current Recording from Cells and Cell-Free Membrane Patches.' Pflugers Arch (1981) vol. 391, pp. 85-100.*

(Continued)

Primary Examiner—William H Beisner
(74) Attorney, Agent, or Firm—The Nath Law Group; Tanya E. Harkins

(57) ABSTRACT

The invention shows a method for patch-clamp experiments on cells or similar structures, where at least one cell is inserted into the lumen of a capillary and is positioned inside the capillary so, that a sufficiently tight seal with a resistance exceeding 1, preferably 10 GigaOhm develops between cell membrane and inner surface of the capillary. Along its length said capillary has at least at one position a smaller inner diameter than the outer diameter of said cell. Preferably the cell is inserted and positioned in the capillary by pressure, suction, sedimentation or centrifugation of a suspension or solution containing said cell. An apparatus for performing experiments using this method is described.

15 Claims, 5 Drawing Sheets

U.S. PATENT DOCUMENTS

Figure 1:
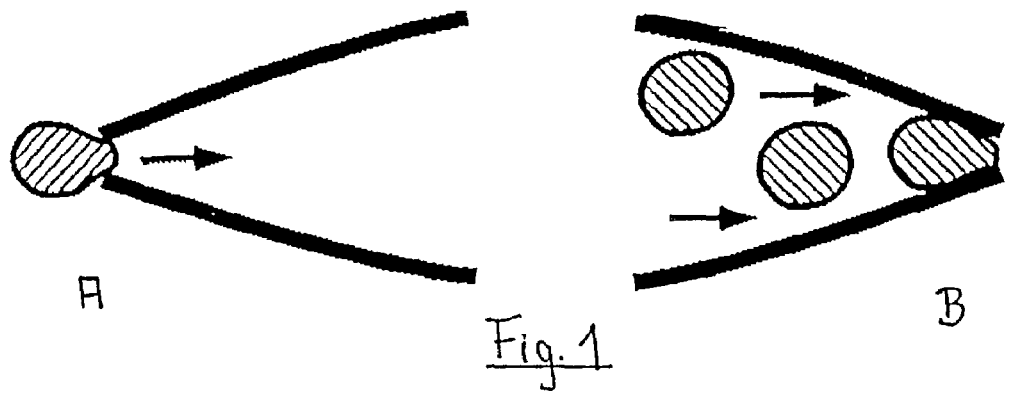

| | | | |
|---|---|---|---|
| 6,048,722 A | * | 4/2000 | Farb et al. ................. 435/287.1 |
| 2003/0080314 A1 | * | 5/2003 | Nisch et al. ................. 252/62.2 |
| 2003/0121778 A1 | * | 7/2003 | Dodgson et al. ............ 204/401 |

FOREIGN PATENT DOCUMENTS

| | | |
|---|---|---|
| DE | 197 12 309 | 5/1998 |
| DE | 197 44 649 | 4/1999 |
| WO | WO 97/17426 | 5/1997 |
| WO | WO 99/66329 | 12/1999 |
| WO | WO 0020554 A1 * | 4/2000 |
| WO | WO 01/48475 A1 | 7/2001 |

OTHER PUBLICATIONS

Hamill, O. P., et al., "Improved Patch-Clamp Techniques for High-Resolution Current Recording from Cells and Cell-Free Membrane Patches". Pflügers Archiv, vol. 391, 1981, pp. 85-100.

Danker, T., et al., "Nuclear hourglass technique: An approach that detects electrically open nuclear pores in Xenopus laevis oocyte", *PNAS*, pp. 13530-13535, vol. 96, No. 23 (1999).

* cited by examiner

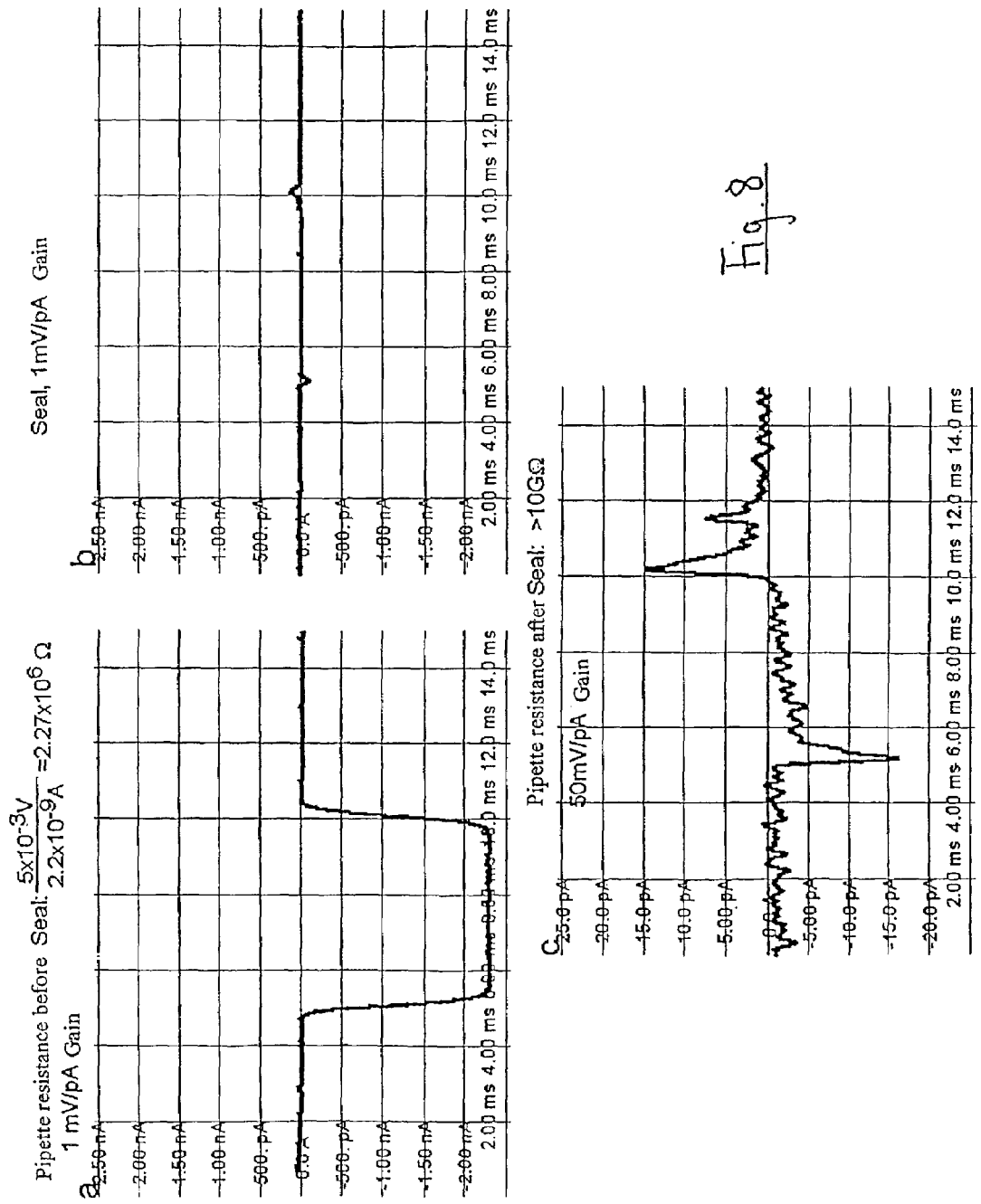

METHOD AND APPARATUS FOR PATCH-CLAMP MEASUREMENTS ON CELLS

The invention relates to a method for measurements on cells or similar structures with the patch-clamp technique and an apparatus for these measurements.

Living cells create an inner microenvironment by surrounding themselves with a lipid membrane thereby securing the function of cellular mechanisms. These lipid membranes are practically impermeable to charged particles. Therefore specialized embedded transport proteins carry ions across the membrane. They represent the basis for a variety of physiological functions including electric excitability of cells, transport of substances across membranes or cell layers and several electrical and chemical signals in cells.

Cell biology research has been revolutionized by the patch-clamp method developed by Sakmann and Neher 1981. The patch-clamp technique permits the direct measurement of currents through ion transporters with high time resolution. In fact this method is the only technique that can measure conformational changes of single specialized protein molecules in real time at a time resolution of a few milliseconds. This allows for example to assess the action of signal molecules or pharmacological agents directly on the target protein. Furthermore, the technique allows to exactly control the electrical and chemical environment of a membrane and the application of signaling molecules, drugs etc. to both sides of the membrane.

This technique can examine a variety of transport proteins including electrogenic ion transporters of organic and anorganic ions, selective and nonselective ion channels and other pore-inducing membrane proteins. Among the ion channels are voltage-gated, ligand-gated and store-operated channels, that are or are not selective for $Na^+$, $K^+$, $Ca^{2+}$ and $Cl^-$. Even charge movements inside a membrane-associated protein can be measured (gating charges). This makes all membrane associated proteins accessible to the technique including receptors, enzymes, and their interaction with other proteins or charged molecules. Ion channels are distributed throughout tissues in a specific manner and are characterized by a great diversity of function. They are therefore ideal targets for pharmacological compounds to manipulate tissue-specific functions. Examples for such compounds are diuretics, antidiabetics, antiepileptics, local anesthetics, antiarrhytmics, some antibiotics etc. The patch-clamp technique represents an extremely sensitive method to assay the biological action of such compounds. The major disadvantage of the method is the complicated experimental procedure, the required manual manipulation and the resulting low throughput of test compounds and transport proteins.

The patch-clamp techniques exists in several different modes. All these modes require micromanipulation. Under microscopic visual control a cell is mechanically approached with a glass micropipette and attached to the pipette by suction. This leads to a electrically tight bond between cellular membrane and pipette tip, a prerequisite for low-noise high-resolution recording of tiny currents. With different modes of the technique currents either through the membrane patch in the pipette tip or through the opposed membrane layer are recorded.

The tight bond between cellular membrane and glass capillary is often referred to as "seal". Different seal qualities allow the experimental study of different cell types and ionic current magnitudes. In 1980 Neher and Sakman described a method to achieve a novel quality of seals, namely so-called gigaseals. This discovery was awarded the Nobel prize in 1991 and the gigaseals allowed for the first time the precise measurement of ionic currents in the picoampere range in small mammalian, human, insect and other cells. In the 1981 publication the group of Neher and Sakman wrote:

"The extracellular patch clamp technique has allowed, for the first time, the currents in single ionic channels to be observed (Neher and Sakmann, 1976). In this technique a small heat polished glass pipette is pressed against the cell membrane, forming an electrical seal with a resistance of the order of 50 MegaOhm (Neher et al., 1978). The high resistance of this seal ensures that most of the currents originating in a small patch of membrane flow into the pipette, and from there into current-measurement circuitry. The resistance of the seal is important also because it determines the level of background noise in the recordings.

Recently it was observed that tight pipette-membrane seals, with resistances of 10-1000 GOhm, can be obtained when precautions are taken to keep the pipette surface clean, and when suction is applied to the pipette interior (Neher 1981). We call these seals "giga-seals" to distinguish them from the conventional, megaohm seals . . .

Gigaseals are also mechanically stable . . .

the membrane patch can be disrupted keeping the pipette cell-attached. This provides a direct low resistance access to the cell interior which allows potential recording and voltage clamping of small cells" (Hamill, Marty, Neher, Sakmann, Sigworth, Pflügers Arch. 391:85-100, 1981).

A "gigaseal" is obtained when the electric resistance after approaching the cell with the pipette tip and suction reaches the Gigaohm range. The usual resistance of several 10 GigaOhm indicates that even small ions like protons are unable to pass between membrane and glass surface. It was previously assumed that such gigaseal has to form between the membrane and the rim of the pipette tip that is approached to the membrane by mechanic force and hydraulic suction. With this gigaseal modern operational amplifiers allow measurements of directed currents in the range down to 100 fA ($10^{-13}$ A). In any case the currents measured represent the sum of ion transport across the membrane plus leak currents through the apparatus and preparation.

The patch-clamp technique is extremely slow and requires highly qualified personnel especially because of the required micromanipulations. Approaching single cells on a microscope stage with the micromanipulator and applying suction to seal the pipette requires a high level of dexterity and experience with mechanical properties of a given cell and its micromanipulation. E.g. the mechanical force applied before suction is critical for the bonding of membrane and pipette tip. Furthermore, the seal is mechanically unstable and can be lost by mechanical perturbation and hydraulic turbulence (e.g. solution exchange). A microscope and micromanipulator are required. This prohibits miniaturization and the principally desired arrangement of arrays with multiple pipettes.

The description above explains that for a variety of potential applications of the patch-clamp technique it would be desirable to examine several cells simultaneously and to obtain gigaseals automatically. This is hindered by the fact, that the tip of a micropipette must be brought into close contact with the cell membrane mechanically. The DE-A1-197 44 649 describes an apparatus and a method to examine multiple cells with an array of multiple pipettes. However, in this patent application the same principle (as mentioned above) of mechanical movement of the pipette array towards the cell membrane is used. The WO 99/66329 describes an array of pores in a thin planar substrate in order to apply cells and examine multiple cells simultaneously. Manufacturing such porous substrates is complicated and expensive and the adherence of cells to multiple pores is arbitrary, difficult to achieve and to control. Seals of cells with the surface of a planar substrate are mechanically unstable and are easily lost by solution exchanges. Furthermore, in all planar arrangements of pores like in the WO 99/66329 or in other transepithelial measuring apparatuses known to a person skilled in the art (e.g. Ussing chambers) the experiment is already disturbed if some of the pores are not tightly sealed with cells. The leaky pores conduct serious leak currents several orders of magnitude larger than the currents through ion transporters to be measured. In such arrangements serious problems arise with electrical crosstalk between pores, especially from leaky pores. The large electric capacitance can cause electrical noise and disturbances thereby reducing the time resolution of the measurement. This is, particularly critical when measuring voltage-gated ion channels.

U.S. Pat. No. 6,048,722 (corresponding to WO 97/17426) describes a cellular physiology workstation for automated data acquisition and perfusion control. The apparatus holds a *Xenopus Oocyte* inside a Pasteur pipette tip to form a seal between the oocyte membrane and glass. The resistance of such seal will not exceed 100-200 MegaOhm. *Xenopus Oocytes* are—in contrast to mammalian cells—rather large. Their outer diameter reaches >1 mm. Therefore they have a huge membrane area and contain several orders of magnitude more ion channels than other cells resulting in ionic currents in the range of several hundred to 1000 nanoAmperes. Therefore, a so-called high resistance seal (in the order of 10-200 MegaOhm) is sufficient to measure large currents in *Xenopus Oocytes*. However, these cells are of amphibian origin and therefore of limited use for the study of ion channel function in mammalian and human cells. In mammalian cells that typically have a diameter ranging from 5-50 micrometers the ionic currents typically only reach one to several hundred picoamperes. In order to measure such tiny currents, the resistance of the seal must be several orders of magnitude higher than for *Xenopus Oocytes*, namely in the range of 1-1000, preferably 10-1000 GigaOhm. As mentioned above, a person skilled in the art did assume that the edge or rim of a glass pipette must be pressed against the cell membrane in order to obtain such a gigaseal. This is also evident from U.S. Pat. No. 6,048,722 that describes the additional, conventional use of biosensors including patch clamp pipettes and injection needles inside the recording chamber. This also requires additional micromanipulation with probes like electrodes, needles and patch clamp pipettes inside the recording chamber for holding of the *Xenopus oocyte*. These requirements lead to the same disadvantages as mentioned above.

In summary, a person skilled in the art did previously assume that a gigaseal has to form between the cell membrane and the rim of a pipette tip that is approached to the membrane by mechanic force and hydraulic suction.

As a consequence it is the object of the present invention to avoid the disadvantages of the state of the art technique. It shall represent a novel approach to achieve gigaseals between membrane and recording chamber or holding substrate required for the patch-clamp technique. It shall increase the mechanical stability of those seals. The need for visual microscopic control shall be eliminated. The invention shall achieve a small electric capacitance of the recording preparation, resulting in small dielectric fluctuations (noise) and a high time resolution of the measured signal. It shall allow measurements in multiple cells simultaneously and/or in rapid order with the patch clamp technique. The apparatus shall be easily automated and assembled using simple or already existing parts. The apparatus shall be miniaturized in order to arrange multiple recording preparations in parallel and integrate the apparatus into existing laboratory robot systems. The apparatus shall arrange multiple recording preparations independently in a way that recording chambers are arranged in a flexible array and chambers containing cells prepared for recording can be easily replaced and moved in said array. Multiple recording preparations shall be electrically shieldable from each other.

The present invention at least partly solves the problems described above with the method for measurements on cells or similar structures with the patch-clamp technique wherein at least one cell is introduced into the inner lumen of a capillary that along the length of the capillary at least at one position has a smaller inner diameter than the outer diameter of said cell, said cell is positioned inside said capillary at said site forming a so-called giga-seal between cell membrane and inner surface of said capillary with an electric resistance of at least 1 GigaOhm, preferably at least 10 GigaOhm, and a patch-clamp experiment is subsequently performed on said cell, as well as the apparatus for experiments on cells or similar structures with the patch-clamp method, especially for application of the method described in any of the preceding claims, comprising at least one capillary that along its length has at least at one site a smaller inner diameter than the outer diameter of a cell and that is designed to hold and position at least one cell in its lumen and allow formation of a so-called giga-seal between cell membrane and inner surface of said capillary with an electric resistance of at least 1 GigaOhm, preferably at least 10 GigaOhm, at least one device designed to introduce said cell into the capillary lumen and position said cell and eventually other devices required to perform a patch-clamp experiment. Preferred embodiments of the method and/or the apparatus are also a method wherein said cell is introduced and positioned in the capillary by flushing or sucking a suspension or solution containing the cell into the capillary; wherein said cell is introduced and positioned in the capillary by centrifugation and/or sedimentation applied to the suspension or solution containing said cell; wherein said capillary is a glass capillary; wherein said capillary is a so called micropipette; wherein said smaller inner diameter is below 50 μm, preferably below 10 μm; wherein said cell has a diameter below 100 μm, preferably below 50 μm, wherein diameters from 30 μm to 3 μm are further preferred; wherein said cell or said suspension or solution containing said cell is introduced into said capillary by passing it through a preferably sterile-filtered liquid or solution, especially a physiological salt solution; wherein prior to the passing step said preferably sterile-filtered liquid or solution is filled into the capillary, thereby covering at least the position where the gigaseal will take place; wherein the position of said cell inside the capillary is controlled before or during a patch-clamp experiment, preferably by measuring pressures or flows or electric resistance or using optical signals, preferably laser light, after positioning of a cell inside the capillary lumen; and/or wherein said cell is removed from the capillary after the patch-clamp experiment, and the capillry is cleaned, preferably by flushing it with an appropriate solvent or chemical. Additional preferred embodiments of the method and/or the apparatus show use of a capillary, a capillary and kit, such as the use of a capillary, preferably a glass capillary, preferably a micropipefte, that along the length of the capillary at least at one position has a smaller inner diameter than the outer diameter of a cell, for performing the instant methods; a capillary, preferably glass capillary, preferably micopipete, having at least at one position a diameter smaller than 100 μm, having an inner surface clean enough for providing a giga-seal in a patch-clamp experiment, that capillary being sealed in a sterile containment or packaging; and/or a kit for performing the instant methods, comprising at least one capillary.

The present invention provides a method where a cell is positioned in the lumen of a capillary and a sufficiently tight seal with a resistance exceeding 1 GigaOhm, preferably 10 GigaOhm is obtained between the cell membrane and the inner wall of the capillary. After achievement of the gigaseal a patch clamp experiment can be performed. The capillary is tapered in a way that it has along the length of the capillary at least at one site a smaller inner diameter than the outer diameter of the cell to be measured.

Taper means a form of the capillary that allows holding a cell that is moved along the length of the capillary and avoids the passage of that cell. Taper can also mean a conical form of the capillary inner wall that encloses that cell circumferentially and allows for a close contact between the inner surface of the capillary and the cell surface. Therefore capillaries will be constructed with a preferentially round inner cross section that narrows along its length to a taper or nozzle in order to hold and position the cell and reach a tight seal between the cell surface and the inner surface of the tapered pipette. Obviously the inner diameter, form and steepness of the taper can be varied to allow for different cell diameters. By using very small inner diameters in the taper very small cells or subcellular membrane structures can be positioned and held, for example mitochondria, lysosomes or bacteria. These structures have so far not been accessible directly with the patch-clamp method, since they are usually too small for light microscopy and micromechanic manipulations. Therefore the term "cell" in the present invention includes any biological or artificial structure surrounded by a lipid membrane.

In the present invention the term "positioning" describes any fixation of the cell in the taper or the capillary sufficient for patch-clamp experiments where a sufficiently tight bond or seal with a resistance exceeding 1, preferably 10 GigaOhm is achieved between cell membrane and inner surface of the capillary wall.

It was surprising that a gigaseal—as required for measurements of ionic currents in small cells (e.g. mammalian cells, human, plant, insect cells)—can be obtained between the inner surface of a capillary lumen, and a cell membrane and that a patch clamp experiment can be performed on such cells after permeabilizing one side of the cell membrane and that additional probes like patch-clamp pipettes or injection needles are unnecessary to perform such experiments. With the invention the mere positioning of the cell in the narrow part of the capillary is sufficient and no additional devices like needles, patch-clamp pipettes or micromanipulators are required for obtaining a gigaseal. Further, the gigaseals obtained according to the invention are mechanically stable and can resist hydraulic and mechanical perturbations. It is routinely possible to remove the capillaries containing sealed cells from the holder of the capillary and move it to another holder without losing the gigaseal. Gigaseals are also resistant to mechanical vibrations, e.g. tapping against the capillary. Liquid can be flushed into the capillary using a narrow tube without breaking the seal.

The length of the capillary is not critical for the present invention. Capillaries of entirely different length can be used. In a preferred embodiment the capillary is at least as long that the cell is positioned entirely inside the capillary.

The above description shows that the narrow part or taper of the capillary can be realized in different ways. In a simple, preferred embodiment the entire capillary is tapered so that the inner diameter decreases gradually or stepwise along the length of the capillary. In this embodiment the cell will be positioned where the inner crossection diameter of the capillary taper approaches the outer cell diameter. In another preferred embodiment the narrowest crossection will be located at one end of the capillary, and the cell will be introduced into the capillary from the other end, so that the cell will be positioned and sealed inside the capillary close to the narrow opening.

In another preferred embodiment the taper will be located at one end, and the cell will be introduced into the capillary from the other end, so that the cell will be positioned and sealed in the narrow opening and part of the cell protrudes from that opening. This allows a rapid exchange of solutions at the protruding part of the membrane.

In a preferred embodiment the tapered capillaries can be so-called mircopettes similar to the various forms of micropipettes used for conventional patch-clamp experiments. A person skilled in the art knows how to fabricate and form such micropipettes. Typically micropipettes are pulled from glass capillaries after (at least local) heating by separation of both ends of the capillary in the melted middle section. The melting guarantees the required clean surface of the pipette material in order to obtain gigaseals.

In a preferred embodiment the capillaries or micropipettes can be made from different non-conductive materials such as plastics (e.g. polystyrene). In another preferred embodiment of the invention the capillaries or micropipettes are made from glass. Glass has been shown to seal tightly to biological membranes and has good dielectrical properties. Glass is inert to a wide range of chemicals and can be easily cleaned. Furthermore, glass capillaries and micropipettes can be fabricated with a wide range of taper diameters at low cost with standard glass forming technology. Irrespective of the material, in preferred embodiments inner diameters of the taper/opening of the narrowest part below 50 micrometer, especially below 10 micrometer (pm), depending on the diameter of the examined biological structure or cell are used. A preferred lower limit for such diameter is 50 nanometer (nm).

In a preferred embodiment of the invention cells are brought into and positioned inside the capillary by filling or flushing the capillary with a suspension of cells in solution. For example the cell suspension will be filled into the large opening of a micropipette and suction will be applied towards the narrow opening, leading to the positioning of a cell in the taper of the pipette. The positioning is achieved simply by movement of fluid and/or the cell. As soon as the first cell moves into the taper the contact between cell surface and inner wall of the capillary seals the cell to the capillary and blocks the liquid flow. Therefore no additional cells are moved into the taper. The introduction of cells into the capillary and the positioning of a cell in the taper is therefore achieved in a single step. According to the invention it is preferred to apply pressure gradients of 5 mbar (0.5 bar) to 1 bar, especially 5 mbar to 500 mbar.

Alternatively or additionally in another embodiment of the invention the introduction and positioning of cells in the capillary can be achieved by sedimentation. In this case, the capillary is fixed in an upright direction and the cell is positioned by gravity, preferably in addition to the hydraulic flow described above.

Alternatively or additionally in another embodiment of the invention the introduction and positioning of cells in the capillary can be achieved by centrifugation. In this case, a cell suspension is centrifuged into the capillary and the cell is positioned by centrifugal force, preferably in addition to the liquid flow described above. To obtain gigaseal with cells preferably centrifugation at 2 to 20 g is performed. For bacteria and other small membrane structures below 1 micrometer diameter centrifugation at 10 to 500 g is preferable.

Alternatively or additionally in another embodiment of the invention the introduction and positioning of cells in the capillary can be achieved or facilitated by mechanical vibration or by use of an electric field applied longitudinally along the capillary. Another embodiment uses magnetic beads coupled to or enclosed by the cells and positioning of said cell using a magnetic field. Another embodiment uses laser light (optical tweezers) in order to position the cell.

In a preferred embodiment of the invention, at least the tapered part of the capillary is first filled with a physiological solution (preferably cleaned by passage through a sterile filter or by centrifugation). The cell suspension is then layered on top of that solution. Subsequently, cells pass through the clean solution layer towards the taper by means of gravity, centrifugation etc. as described above. Since cells are in most cases heavier than membrane fragments and other typical contaminating particles in a cell suspension, this procedure allows the cells to be "rinsed" while entering the tapered part of the capillary. Furthermore, the probability of an intact cell to enter the narrow taper before any other particle is increased. This effectively reduces the risk of contamination of the inner surface of the pipette taper with particles that would otherwise prevent the subsequent formation of a gigaseal.

In general, it is especially advantageous for preferred embodiements of the invention that the inner surface of the capillary is extremely clean for providing gigaseals, especially gigaseals with very high resistances. As a consequence, it is preferred to produce the capillary, especially at least the tapered/narrow part of such capillary with a very clean inner surface. Further, it is preferred to keep such inner surface extremely clean until the capillary is used for a patch-clamp experiment and even during such patch-clamp experiment.

For producing gigaseals with cells inside capillaries according to the invention it is preferred to fulfil at least one of the following 4 technical requirements. Clearly, it is further preferred to fulfil all 4 technical requirements.
1. Melting, preferably complete melting of the capillary during production of the taper/narrowing for guaranteeing submersion of any dust particles or contaminants beyond the inner surface.
2. Avoidance of contamination of the inner surface by keeping the capillary in an extremely clean environment after production, e.g. by sealing it in a sterile containment under a flow of filtered air (preferably 0.2 micrometer pore size).
3. Avoidance of contamination of the inner surface during the experiment, e.g. by filling at least the taper with a sterile-filtered solution, e.g. a physiological salt solution.
4. Avoidance of contamination of the inner surface during the experiment stemming from contaminating particles in the cell suspension by sedimentation and/or centrifugation of cells through said layer of a sterile-filtered solution.

In preferred embodiments the following parameters are measured in said positioned cell or membrane structure: current in voltage-clamp, voltage in current-clamp, electric resistance, impedance, electric capacity, optic fluorescence, plasmon resonance, mechanic resonance, fluidity and/or rigidity.

In preferred embodiments the positioning of the cell can be verified and/or controlled before performing a patch-clamp experiment. This can be achieved by optical means, for example by analysis of laser light illuminating the taper of the capillary. In this context said cell can be stained with dyes, dye-coupled antibodies, ligands, lipids etc. The dye can be chosen to indicate chemical variations inside the cell or at the cell surface and thus yield biological information in addition to the position of the cell in the capillary, for example chemical changes in the cytosol. Preferably, the positioning of the cell is controlled and verified by measuring pressure and/or flow through the capillary. Changes in pressure and/or flow indicate positioning of a cell in the capillary taper. Pressure and flow can be regulated, preferably automatically, in order to achieve the desired positioning of a cell and the tight seal between membrane and inner capillary surface. Further preferred, the electrical resistance along the capillary is measured in order to assess the position of the cell respective to the taper and to measure the quality of the seal. The positioning forces can then be regulated in order to improve the resistance of the seal. By this means hydraulic or centrifugation forces can he controlled in order to achieve an optimal seal between the membrane of different cell types and the inner capillary surface.

According to the invention a new capillary or micropipette can be used for each patch-clamp experiment. This guarantees a new, extremely clean surface for positioning and sealing a new cell. In another preferred embodiment the capillary is reused after a patch clamp experiment. For this purpose the cell is removed from the capillary by suction/flushing. Subsequently the capillary is cleaned and prepared for another patch-clamp experiment. Cleaning of the capillary is preferably done by flushing with solvents or chemicals. Additionally or alternatively heat and ultrasound can be used to clean the capillary inner surface.

It is obvious to a person skilled in the art that the claimed method can be modified in several ways. For example, solution exchange can be performed on both sides of the cell after sealing said cell to the inner wall of the capillary. Solution exchange can be performed using tubes or outlets for suction and/or flushing etc. Futhermore, the membrane can be permeabilized selectively on one side of the seal. To achieve this, pressure changes, ultrasound, electric voltage jumps or permeabilizing chemicals (e.g. ionophors, tensides, enzymes, solvents) can be used. They can be applied through said solution exchange devices. Selective permeabilization of one membrane surface can render the inner side of the other membrane surface accessible to substances applied to the capillary and can reduce the electric resistance accessing the other membrane surface. According to the invention for rupture of the membrane no additional probes like needles nor mechanical movement of such probes is required.

Obviously a variety of different cell types can be examined with the present method. According to the invention it is preferred to use cells or subcellular structures (as mentioned above) having diameters below 100 μm, preferably below 50 μm. Use of cells or structures with diameters from 30 μm to 3 μm is further preferred.

To name a few, cells that can be examined include Jurkat lymphoma cells, HEK293 cells, Chinese hamster ovary (CHO) cells, primary cells from neuronal tissue like hippocampus, ganglion, neuroendocrine cells etc.; skeletal muscle, smooth muscle, heart muscle, immune cells; epithelia and endothelia etc. Furthermore, cells can be genetically engineered. For example, ion transport proteins can be expressed in cell lines, e.g. CHO cells. In a preferred embodiment genetic material like DNA or RNA can be harvested from the capillary following the patch-clamp experiment.

In another embodiment the presented method can be used to examine artificial or natural lipid vesicles. Preferably ion transport proteins, possibly genetically modified proteins, can be inserted into these vesicles. Furthermore, subcellular membrane structures (e.g. mitochondria, lysosomes, endoplasmic reticulum, nuclei), plant cells and prokaryotic cells (e.g. bacteria) can be examined, since in contrast to the state of the art patch-clamp technique structures with diameters well beyond 1 micrometer can be positioned and sealed.

In a preferred embodiment material is collected/harvested from the positioned cell, possibly proteins, lipids, RNA, DNA, enzymes and other molecules.

The invention further comprises a new apparatus for patch-clamp experiments on cells or other membrane structures preferably for applying the method described above. This apparatus comprises at least one capillary, at least one device for delivering a cell into said capillary lumen and positioning of said cell inside the capillary and eventually other usual devices required to perform a patch clamp measurement. Said capillary is tapered in a way that along the length of the capillary at least one site has a smaller inner diameter than the outer diameter of the cell to be measured. Furthermore the capillary is designed in a way that a cell can be introduced into said capillary lumen and positioned in order to obtain a gigaseal between the cellular membrane and the inner surface of the capillary. The design of the apparatus and its advantages relate directly to the method described above and the method's description is explicit part of the description of said apparatus.

In a preferred embodiment of the invention the apparatus contains devices that allow flushing and draining the capillary lumen with at least one solution or cell suspension. For this purpose liquid containers like reservoirs, tubes for feeding and draining the capillary, pumps for suspensions and solutions, pipettes, valves and pressure/flow gauges can be implemented.

In a preferred embodiment of the invention the flushing/draining devices are complemented or replaced by a device designed to centrifuge the cells into the capillary.

The apparatus may contain devices to measure the electrical resistance (e.g. electrodes preferably made from chloride-silver or carbon fibers and cabling) or devices to analyze optical properties of the cell/capillary system, preferably laser light sources, optical fibers, and light detectors. Said devices can be used in order to control and adjust positioning of the cell inside the capillary.

The advantages of the invention are most obvious in a preferred embodiment of the invention, where multiple tapered capillaries, preferably micropipettes, are used. The capillaries can be arranged preferably in a regularly spaced array. In this way the patch-clamp method can be automated, since cells sealed in capillaries can be examined either simultaneously or in a rapid sequential order.

In the embodiments with multiple capillaries cells can be positioned inside said capillaries in a first step. Since the positioned cells are mechanically protected and firmly sealed, cell-containing capillaries can be transferred in a second step into a measuring device. Furthermore, cell-containing capillaries can be replaced if the sealing attempt or the attempt to open the membrane fails. In this embodiment an array of positioned, sealed and opened cells can be assembled.

In the embodiments with multiple capillaries such capillaries can be easily electrically shielded from each other and from the environment. In this context preferably grounded shields from metal or any other conductive material can be used in closing the capillaries. Such shields e.g. can be in the form of cylindrical tubes partly or completely enclosing the capillaries.

In the embodiments with multiple capillaries preferably multiple liquid containers are used, preferably microwells, that hold suspensions or solutions with cells and compounds. These containers can be wells in a microtiter plate. Preferably the number and arrangement of containers relates to the capillary array. This allows to transfer liquid from a defined well into a corresponding capillary, for example using piston stroke pipettes.

In the embodiments described the capillaries and the liquid containers are preferably arranged or moved in a way, that suspensions or solutions including cell suspensions can be easily transferred into the capillary lumen. The figures and figure descriptions provide examples for such arrangements.

In a preferred embodiment at least one capillary in the apparatus is tapered in a way that along the length of the capillary at least one site has a smaller inner diameter than the outer diameter of the cell to be measured in order to apply the method described in the present invention. The capillary is preferably made of glass and is preferably a micropipette.

The described features and specifications as well as other features and specifications result from the following experimental protocol and the figure descriptions. Different features can be implemented in said experimental protocol or figures alone or in combination.

FIGURES

FIG. 1 is a sketch comparing the positioning of a cell using the regular patch-clamp technique (A) and the invented method (B)

Figure 2:
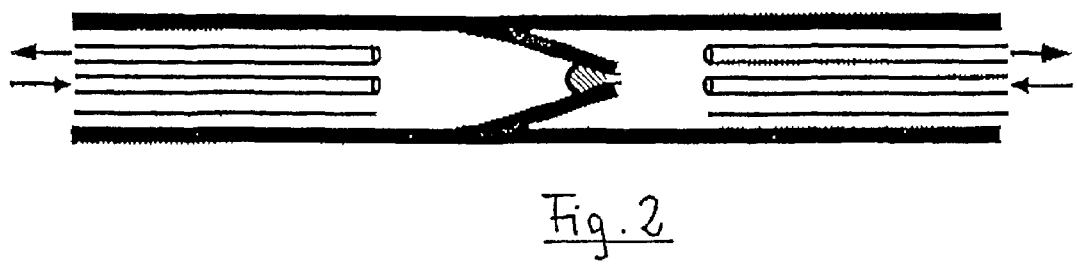

FIG. 2 Sketch of an embodiment of the capillary according to the invention

Figure 3:
Figure 4:
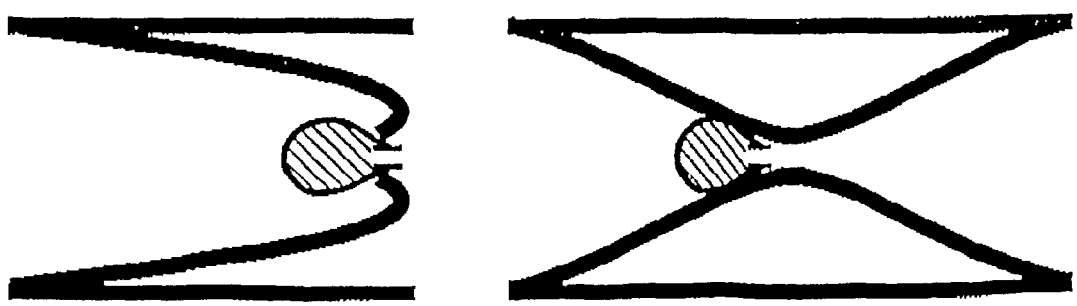
Figure 5:
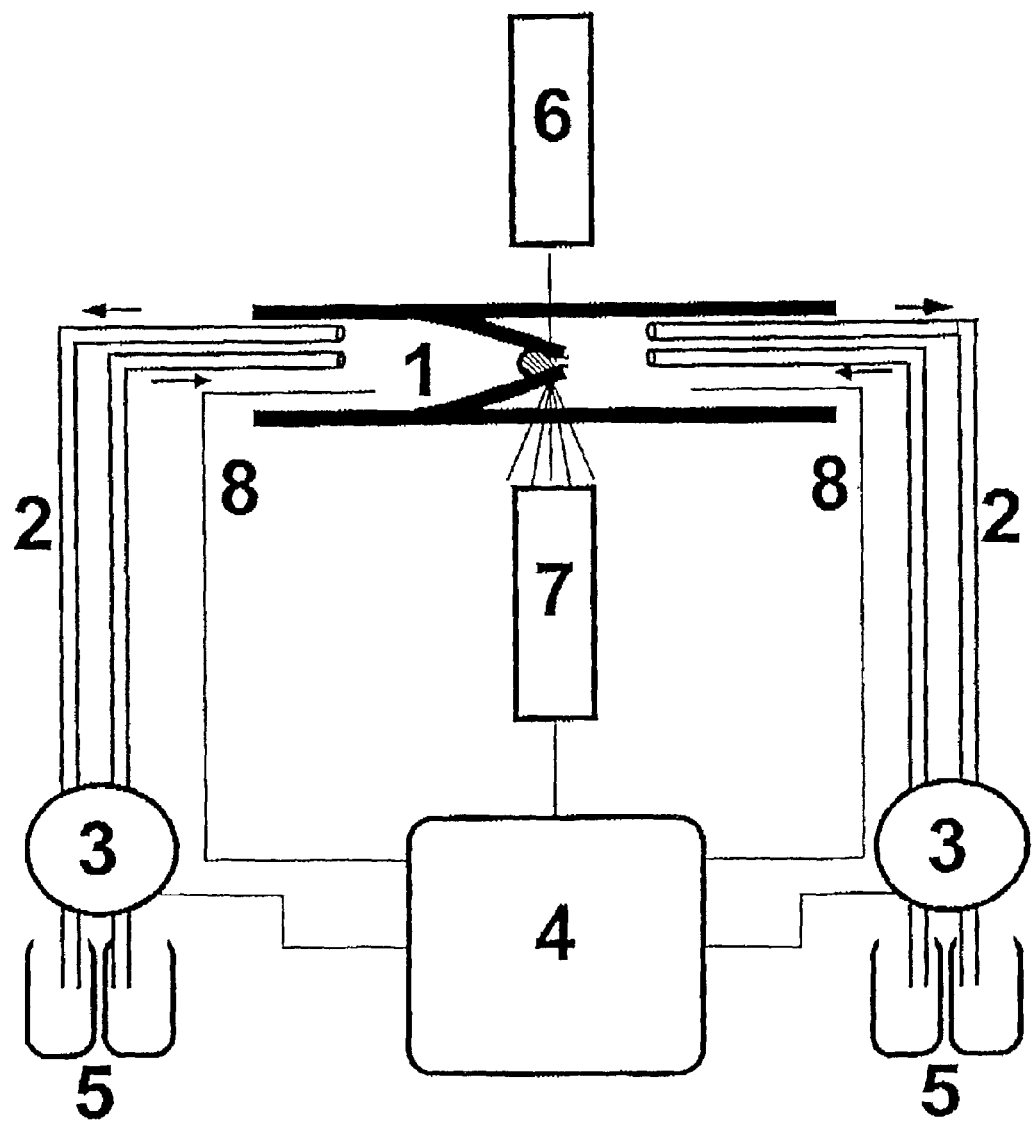

FIG. 3 Sketch of selective permeabilization of one side of the membrane, respectively FIG. 4 Sketches of two other embodiments of capillaries containing cells in the sealed position FIG. 5 Sketch of an apparatus for automated patch-clamping comprising a capillary with cell and additional devices.

Figure 6:
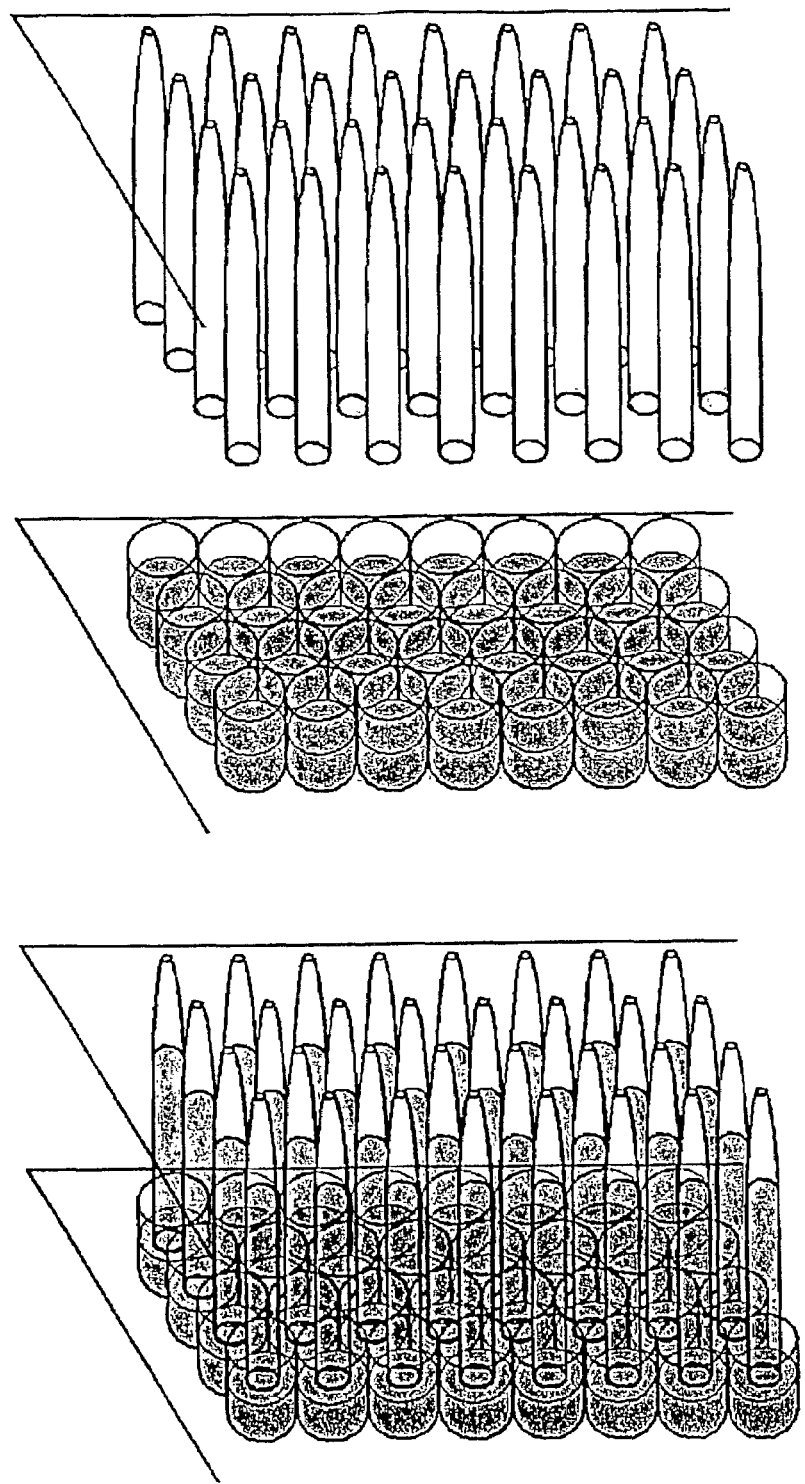
Figure 7:
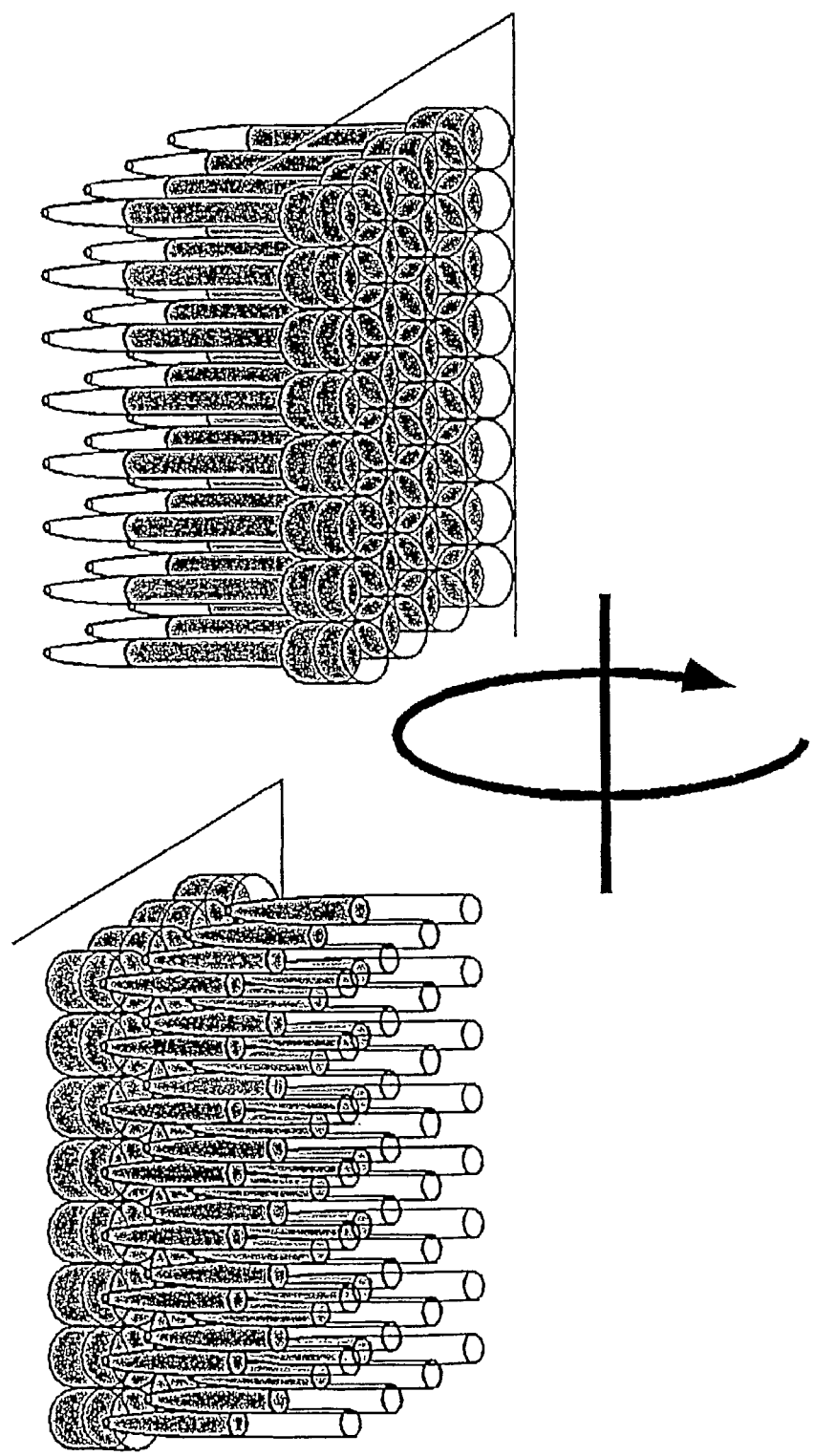

FIG. 6 Sketch of an array of multiple capillaries to perform automated positioning by suction and automated patch-clamping FIG. 7 Sketch of an array of multiple capillaries to perform automated positioning by centrifugation and automated patch-clamping FIG. 8 Current traces in response to voltage steps demonstrating increase of resistance due to gigaseal formation during the positioning of a cell inside a capillary FIG. 1 illustrates the differences between the invented method and the state of the art regular patch-clamp technique. FIG. 1A shows attachment (seal) of a cell to the tip of a micropipette with the conventional patch-clamp method. The seal forms between the rim of the pipette opening and the cell membrane. The arrow indicates the direction of suction/flow, after pressing the pipette tip against the cell and applying vacuum to the pipette interior. FIG. 1B shows positioning and sealing a cell with the invented method. The arrows indicate the direction of flow and/or movement of cells when suspended cells, in FIG. 1B for example three cells, are moved towards the tip of the micropipette. FIG. 1B further shows a cell sealed to the inner wall of the tapered pipette. A patch-clamp experiment can be performed on this cell. In contrast to the state of the art the invented method does not require to move the micropipette towards the cell. The cells are flushed into the pipette lumen and positioned in the taper. This method is not only simple, but also eliminates the need for a microscope to control positioning and a micromanipulator to position the micropipette. This allows in any case to miniaturize and automate the apparatus.

FIG. 2 shows a capillary and a cell positioned and sealed according to the invented method. The capillary is constructed as a thin tube (outer diameter 1.5 mm, inner diameter 1.2 mm) and in the example shown it tapers down to a small opening (0.5-1 µm). In this taper a cell (diameter ≈10 µm) is positioned and its membrane is sealed to the inner surface of the taper preferably consisting of glass. The two small lines in the opening of the taper symbolize permeabilization of the cell membrane on the right side. In both sides of the capillary thin tubes for flushing/draining solutions and suspensions are inserted (outer diameter 0.2 mm, inner diameter 0.1 mm). The arrows indicate direction of liquid flow. These flushing/draining devices can be either used to fill cell suspension into the capillary (left in- and outlet), or to drain cell suspension, for example, after an experiment (left in- and outlet). Furthermore, the tubes can be used for cleaning of the capillary (left and right in- and outlets) or for application of pharmacological substances, membrane permeabilizing chemicals and other compounds (left and right in- and outlets). In addition electrodes are inserted into the capillary lumen (for example chlorided silver wire, outer diameter 0.2 mm) that serve electrical measurements of current and/or voltage and injection of current. The dimensions of the capillary, the taper and the in- and outlets can be adjusted to the respective requirements, e.g. to the diameter of cell types with different size.

FIG. 3 shows how the cell membrane can be permeabilized on both sides of the circumferential seal. I.e., the cell membrane can be rendered permeable either on the narrowing entry side of the taper or on the exit side. The permeabilization is symbolized by double lines. Corresponding information was given in the above description.

FIG. 4 shows two additional, alternative models of tapered capillaries with a cell sealed in the narrow part, respectively. The left panel of FIG. 4 shows a taper, that folds backward exposing a round rim or edge at the narrowest part of the capillary. The right panel shows a capillary with an hourglass-like shape, shown in FIG. 4 in the way that the taper is symmetrically mirrored to both sides of the narrowest position. The features described in FIG. 4 are herewith explicitly claimed as part of the description of the invention.

FIG. 5 shows a sketch of an apparatus according to the invention. A glass capillary 1 formed as a micropipette similar to the model shown in FIG. 2 is shown. In the nozzle-like part of the tapered capillary 1 a cell is positioned for experiments. In- and outlets 2 are inserted in both ends of the capillary lumen at both sides of the cell. These in- and outlets are connected to pumps and pressure/flow gauges 3 that serve to transfer liquids between reservoirs 5 and capillary 1 and measure pressures and/or flow rates. Electrodes 8 are inserted into both sides of the capillary 1. These electrodes are represented by lines below the in/outlets also in (FIG. 2.)

A laser light source 6 and a light detector 7 are shown in FIG. 5. They serve to control positioning and fixation of the cell in capillary 1. All respective elements are electronically connected to a controlling device 4 that contains a computer and records data, performs voltage and/or current clamp (see below), analyzes data, and controls and regulates the apparatus.

FIGS. 6 and 7 show an apparatus, where multiple capillaries are assembled. The capillaries are arranged in a planar, regular array and can be positioned by the apparatus above a respective array of multiple reservoirs. These reservoirs can be microvessels in a microtiter plate like shown in FIGS. 6 and 7. The larger openings of the pipettes point towards the microvessels and can be moved into those vessels. The vessels can be filled with suspensions of cells. In the lower part of FIG. 6 the suspensions are sucked into the pipettes. In FIG. 7 suspended cells are moved towards the pipette tips by centrifugation. For this purpose the pipette array holder is mounted in a rotor. By rotation the centrifugal force moves the cells towards the narrow part of the pipettes. The lower part of FIG. 7 shows another microtiter plate. The vessels in this plate can be filled with solutions of pharmacological substances. The cell-holding pipette array can dip into the vessels in order to test pharmacological compounds. Alternatively or additionally, substances or solutions thereof can be transferred from vessels into cell-holding micropipettes by liquid handling devices, for example pipetting robots.

FIGS. 8 and 9 is discussed in the following description of an experiment.

DESCRIPTION OF AN EXPERIMENT

Patch-clamp micropipettes with dimensions as described in FIG. 2 were pulled from borosilicate glass (Clark Electromedical Instruments, Reading, UK) using a microprocessor controlled puller (Zeitz Instrumente, Augsburg, FRG). Pipette tips were fire polished in the puller down to a tip resistance of 2-3 MegaOhm in an aqueous solution containing 150 mM NaCl. To reduce electric capacitance some pipette tips were coated on their outer surface with silicon rubber or paraffin.

Measurements were performed using an EPC9 patch-clamp amplifier (HEKA, Lambrecht, FRG) for voltage clamp and data aquisition. The data were digitized at 10 kHz and filtered at 2 kHz. Analysis was performed using software from HEKA. "Voltage clamp" means a usual technique for the control of electric parameters during a patch-clamp measurement. A high-resistance feedback-circuitry injects exactly the amount of current into the biological preparation so that the voltage remains at the desired value. The analog circuitry features high time-resolution and permits compensation of capacitive currents, series resistance and leak currents that shall be distinguished from the ionic currents flowing through the examined membrane structures.

The pipette was filled with a sterile-filtered modified Ringer solution containing 145 mM NaCl, 5 mM KCl, 2 mM $CaCl_2$, 1 mM $MgCl_2$, 10 mM glucose and 10 mM HEPES (pH 7,4). The pipette was electrically connected to the pre-amplifier via a silverwire coated with AgCl. 100-500 Jurkat T cells (ATCC, VA, USA) with a diameter of approximately 5 µm suspended in approx. 10 µm RPMI medium were introduced into the micropipette using a fine glass tube. The pipette tip was then dipped into a bath containing the ground electrode. Resistance was measured with a 5 mV voltage step (see FIG. 8a). A pressure of 0.5 bar was applied to the pipette flushing the cells towards the pipette tip. The pressure gradient was removed as soon as the electric resistance of the pipette increased indicating the positioning of a cell in the pipette taper (FIG. 8b).

This type of experiment could reproduce gigaseals between pipette interior and cell membrane. Like with the conventional patch-clamp method the electric resistance was in the range >10 Gigaohm (see FIG. 8c).

This experiment further demonstrates that the cell is positioned in the narrowing taper of the pipette. Application of either a short pressure pulse (1 bar, 200 ms) or a voltage jump (500 mV, 0.1 ms) perforated the cell membrane on one side. This was obvious from the increase in capacitive charge movements (current transients). The gigaseal was typically stable over extended time periods (10->60 min.) and was even resistant to mechanical vibrations purposely applied to the micropipette.

The experiment described here shows unequivocally, that by introducing a cell into a glass capillary featuring a narrow taper a stable gigaseal can be obtained between cell membrane and the inner surface of the pipette wall. The resistance and stability of the seal are high enough to achieve the advantages described.

The invention claimed is:

1. Method for measurements on cells or similar structures with the patch-clamp technique, comprising:

introducing at least one cell having a outer diameter below 100 μm into the inner lumen of a capillary having openings and a capillary taper, said capillary taper ending in an opening and having at least at one position having an inner diameter smaller than the outer diameter of said cell, wherein the capillary has a clean inner surface at least in said capillary taper, and wherein the inner diameter of said capillary taper is less than 10 μm; positioning said cell at a site inside said capillary taper, wherein said cell circumferentially is at least in contact with the inner surface of the capillary taper and at said site forming a giga-seal between cell membrane and inner surface of said capillary taper with an electric resistance of at least 10 GigaOhm; and performing a patch-clamp experiment on said cell wherein said electric resistance is measured inside said capillary taper at the site of the giga-seal.

2. The method according to claim 1, wherein said cell is introduced and positioned in the capillary by flushing or sucking a suspension or solution containing the cell into the capillary.

3. The method according to claim 2, wherein said cell, said suspension or solution containing said cell is introduced into said capillary by passing it through a liquid or solution.

4. The method according to claim 3, wherein said pass through liquid or solution is a sterile-filtered liquid or solution, and said method further comprises prior to the passing step filling said sterile-filtered liquid or solution into said capillary, thereby covering at least to the position where the giga-seal will take place.

5. The method according to claim 3, wherein said cell or said suspension or solution containing said cell is introduced into said capillary by passing it through a physiological salt solution.

6. The method according to claim 1, wherein said cell is introduced and positioned in the capillary by centrifugation and/or sedimentation applied to the suspension or solution containing said cell.

7. The method according to claim 1, wherein said capillary is a glass capillary.

8. The method according to claim 1, wherein said capillary is a micropipette.

9. The method according to claim 1, further comprising controlling the position of said cell inside said capillary before or during the patch-clamp experiment by performing a step after positioning of said cell inside the capillary lumen.

10. The method according to claim 9, wherein the position of said cell inside the capillary is controlled by measuring pressures or flows or electric resistance or using optical signals.

11. The method according to claim 10, wherein the position of said cell inside the capillary is controlled by means of laser light.

12. Method according to claim 1, further comprising removing said cell from said capillary after the patch-clamp experiment and cleaning said capillary.

13. The method according to claim 12, wherein the capillary is cleaned by flushing it with an appropriate solvent or chemical.

14. The method according to claim 1, wherein said cell has a diameter below 50 μm.

15. The method according to claim 1, wherein said cell has a diameter from 30 μm to 3 μm.

* * * * *